United States Patent
Kang et al.

(10) Patent No.: US 11,000,192 B2
(45) Date of Patent: May 11, 2021

(54) BIO-INFORMATION MEASURING APPARATUS, BIO-INFORMATION MEASURING METHOD, AND CASE APPARATUS FOR THE BIO-INFORMATION MEASURING APPARATUS

(71) Applicant: SAMSUNG ELECTRONICS CO., LTD., Suwon-si (KR)

(72) Inventors: Jae Min Kang, Seoul (KR); Yong Joo Kwon, Yongin-si (KR); Sang Yun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 451 days.

(21) Appl. No.: 16/026,765

(22) Filed: Jul. 3, 2018

(65) Prior Publication Data

US 2019/0125198 A1 May 2, 2019

(30) Foreign Application Priority Data

Oct. 31, 2017 (KR) ........................ 10-2017-0144141

(51) Int. Cl.
*A61B 5/00* (2006.01)
*A61B 5/021* (2006.01)
*A61B 5/024* (2006.01)
*A61B 5/02* (2006.01)

(52) U.S. Cl.
CPC .......... *A61B 5/02108* (2013.01); *A61B 5/002* (2013.01); *A61B 5/02007* (2013.01); *A61B 5/02427* (2013.01); *A61B 5/02433* (2013.01); *A61B 5/6843* (2013.01); *A61B 5/746* (2013.01); *A61B 5/6898* (2013.01); *A61B 2562/0233* (2013.01); *A61B 2562/0247* (2013.01)

(58) Field of Classification Search
CPC combination set(s) only.
See application file for complete search history.

(56) References Cited

U.S. PATENT DOCUMENTS

| | | | |
|---|---|---|---|
| 8,761,853 B2 | 6/2014 | Thaveeprungsriporn et al. | |
| 9,274,652 B2 | 3/2016 | Chang et al. | |
| 2006/0079741 A1 | 4/2006 | Kanayama | |

(Continued)

FOREIGN PATENT DOCUMENTS

| | | |
|---|---|---|
| EP | 1647225 A1 | 4/2006 |
| EP | 2839778 A1 | 2/2015 |

(Continued)

OTHER PUBLICATIONS

Communication dated Apr. 1, 2019, issued by the European Patent Office in counterpart European Patent Application No. 18201571.9.

*Primary Examiner* — Joel F Brutus
(74) *Attorney, Agent, or Firm* — Sughrue Mion, PLLC

(57) ABSTRACT

An apparatus for measuring bio-information includes a pulse wave sensor configured to emit light having a plurality of wavelengths onto an object, and to detect a multi-wavelength pulse wave signal from the object; and a processor configured to obtain a contact pressure signal based on the multi-wavelength pulse wave signal, the contact pressure signal indicating a pressure between the object and the pulse wave sensor, and to generate information regarding a measurement state of the object based on the contact pressure signal.

24 Claims, 14 Drawing Sheets

(56) References Cited

U.S. PATENT DOCUMENTS

| | | |
|---|---|---|
| 2007/0268269 A1 | 11/2007 | Chang et al. |
| 2008/0139905 A1 | 6/2008 | Kanayama |
| 2013/0041237 A1 | 2/2013 | Kanayama |
| 2015/0057508 A1 | 2/2015 | Narusawa |
| 2015/0141774 A1* | 5/2015 | Ogawa ............... A61B 5/14552 600/301 |
| 2015/0342527 A1 | 12/2015 | Karnik et al. |
| 2015/0374249 A1 | 12/2015 | Elliott et al. |
| 2016/0015301 A1 | 1/2016 | Elliott et al. |
| 2016/0198962 A1* | 7/2016 | Park .................... A61B 5/0295 600/480 |
| 2016/0220194 A1 | 8/2016 | Kang et al. |
| 2016/0278645 A1 | 9/2016 | Yoon |
| 2016/0301150 A1* | 10/2016 | Choi ..................... H05K 1/148 |
| 2017/0095168 A1* | 4/2017 | Kwon ................. A61B 5/1172 |
| 2017/0100038 A1 | 4/2017 | Narusawa |
| 2017/0119293 A1 | 5/2017 | Matsui |

FOREIGN PATENT DOCUMENTS

| | | |
|---|---|---|
| JP | 2007-330708 A | 12/2007 |
| KR | 10-2006-0081178 A | 7/2006 |
| KR | 10-2007-0097415 A | 10/2007 |
| KR | 10-0866484 B1 | 11/2008 |
| KR | 10-2015-0119855 A | 10/2015 |
| KR | 10-2016-0094218 A | 8/2016 |
| KR | 10-2016-0115017 A | 10/2016 |
| KR | 10-2017-0040034 A | 4/2017 |

* cited by examiner

BIO-INFORMATION MEASURING APPARATUS, BIO-INFORMATION MEASURING METHOD, AND CASE APPARATUS FOR THE BIO-INFORMATION MEASURING APPARATUS

CROSS-REFERENCE TO RELATED APPLICATION(S)

This application claims priority from Korean Patent Application No. 10-2017-0144141, filed on Oct. 31, 2017, in the Korean Intellectual Property Office, the entire disclosure of which is incorporated herein by reference for all purposes.

BACKGROUND

1. Field

Apparatuses and methods consistent with exemplary embodiments generally relate to a bio-information measuring apparatus, a bio-information measuring method, and a case apparatus for the bio-information measuring apparatus, and more particularly to technology for monitoring and indicating a state of bio-information measurement by using an apparatus for measuring bio-information in a non-invasive manner.

2. Description of the Related Art

A method of measuring blood pressure in a non-invasive manner without damaging a human body includes a method of measuring blood pressure by using a cuff-based measurement method and a method of measuring blood pressure by measuring pulse waves without using a cuff.

In the cuff-based method of measuring blood pressure, there is a Korotkoff-sound method which measures blood pressure by winding a cuff around an upper arm, increasing and then decreasing pressure in the cuff, and monitoring an audible sound of blood vessels through a stethoscope; and an Oscillometric method, which is employed by an automated device, and measures blood pressure by winding a cuff around an upper arm, continuously measuring pressure in the cuff after increasing and gradually decreasing cuff pressure, and measuring blood pressure based on a point where a pressure signal is changed substantially.

In a cuffless method of measuring blood pressure, there is a method of estimating blood pressure by calculating a Pulse Transit Time (PTT), and a Pulse Wave Analysis (PWA) method of estimating blood pressure by analyzing a pulse wave shape.

SUMMARY

One or more exemplary embodiments provide a bio-information measuring apparatus, a bio-information measuring method, and a case apparatus for the bio-information measuring apparatus, in which bio-information such as blood pressure may be accurately measured without using a cuff.

According to an aspect of an exemplary embodiment, there is provided an apparatus for measuring bio-information, including: a pulse wave sensor configured to emit light having a plurality of wavelengths onto an object, and to detect a multi-wavelength pulse wave signal from the object; and a processor configured to obtain a contact pressure signal based on the multi-wavelength pulse wave signal, the contact pressure signal indicating a pressure between the object and the pulse wave sensor, and to generate information regarding a measurement state of the object based on the contact pressure signal.

The pulse wave sensor may include one or more sources configured to emit the light having the plurality of wavelengths onto the object; and one or more detectors configured to detect the multi wavelength pulse wave signal from the object.

The one or more light sources may include at least one from among a light emitting diode (LED), a laser diode (LD), and a fluorescent element.

The processor may obtain a differential signal between detected multi-wavelength pulse wave signals, and obtain the contact pressure signal based on the differential signal.

The plurality of wavelengths may include two or more from among an infrared wavelength, a red wavelength, a green wavelength, and a blue wavelength.

The processor may obtain the differential signal between a pulse wave signal having the blue wavelength and pulse wave signals having other wavelengths among the plurality of wavelengths.

The processor may obtain the contact pressure signal based on a ratio of a first differential signal, which is obtained by differentiating the pulse wave signal having the blue wavelength from a pulse wave signal having the green wavelength, and a second differential signal which is obtained by differentiating the pulse wave signal having the blue wavelength from a pulse wave signal having the red wavelength.

The processor may determine whether a contact state between the object and the pulse wave sensor is normal based on the contact pressure signal, and based on a determination that the contact state is not normal, the processor may generate information regarding the pressure between the object and the pulse wave sensor.

The apparatus may further include an output part configured to output the generated information under control by the processor.

The processor may measure the bio-information based on the multi-wavelength pulse wave signal and the contact pressure signal.

The processor may obtain a feature point based on the multi-wavelength pulse wave signal and the contact pressure signal, and measure the bio-information by using the feature point and a measurement model.

The bio-information may include one or more from among blood pressure, vascular age, degree of arteriosclerosis, aortic pressure waveform, vascular compliance, stress index, and degree of fatigue.

According to an aspect of another exemplary embodiment, there is provided a method of measuring bio-information, the method including: emitting light having a plurality of wavelengths onto an object; detecting a multi-wavelength pulse wave signal from the object; obtaining a contact pressure signal based on the multi-wavelength pulse wave signal, the contact pressure signal indicating a pressure between the object and a pulse wave sensor; and generating information regarding a measurement state of the object based on the contact pressure signal.

The obtaining may include: obtaining a differential signal between detected multi-wavelength pulse wave signals; and obtaining the contact pressure signal based on the differential signal.

The plurality of wavelengths may include two or more from among an infrared wavelength, a red wavelength, a green wavelength, and a blue wavelength.

The obtaining the differential signal may include obtaining the differential signal between a pulse wave signal having the blue wavelength and pulse wave signals of other wavelengths among the plurality of wavelengths.

The obtaining the contact pressure signal based on the differential signal may include obtaining the contact pressure signal based on a ratio of a first differential signal, which is obtained by differentiating the pulse wave signal having the blue wavelength from a pulse wave signal having the green wavelength, and a second differential signal which is obtained by differentiating the pulse wave signal having the blue wavelength from a pulse wave signal having the red wavelength.

The generating the information regarding the pressure may include: determining whether a contact state between the object and the pulse wave sensor is normal based on the contact pressure signal; and based on a determination that the contact state is not normal, generating information regarding the pressure between the object and the pulse wave sensor.

The method may further include outputting the generated information.

The method may further include measuring the bio-information based on the multi-wavelength pulse wave signal and the contact pressure signal.

According to an aspect of still another exemplary embodiment, there is provided a bio-information measuring apparatus, including: a pulse wave sensor configured to emit light having a plurality of wavelengths onto an object, which is in contact with the pulse wave sensor, and to detect a multi-wavelength pulse wave signal from the object; a communicator configured to communicate with a case apparatus, which is configured to accommodate the bio-information measuring apparatus, and to receive contact position information of the object from the case apparatus, the contact position information indicating a contact position of the object with respect to the pulse wave sensor; and a processor configured to generate a measurement state of the object based on the contact position information.

The processor, in response to determining that the contact position of the object not being in a normal range based on comparison between the contact position information and reference position information, may generate information on the contact position.

The apparatus may further include an output part configured to output the generated information.

The processor may obtain a contact pressure signal based on the multi-wavelength pulse wave signal, the contact pressure signal indicating a pressure between the object and the pulse wave sensor, and generate the measurement state further based on the contact pressure signal.

The plurality of wavelengths may include two or more from among an infrared wavelength, a red wavelength, a green wavelength, and a blue wavelength, and the processor may obtain the contact pressure signal by using a differential signal obtained by differentiating a pulse wave signal having the blue wavelength, among detected multi-wavelength pulse wave signals, from pulse wave signals having other wavelengths among the plurality of wavelengths.

The processor may measure bio-information of the object by using the multi-wavelength pulse wave signal and the contact pressure signal.

According to an aspect of still another exemplary embodiment, there is provided a case apparatus for accommodating a bio-information measuring apparatus, the case apparatus including: a main body configured to accommodate the bio-information measuring apparatus, the main body including a guide groove; a position sensor disposed around the guide groove and configured to obtain a contact position of an object which comes into contact with a pulse wave sensor of the bio-information measuring apparatus; a processor which is embedded in the main body, the processor configured to receive sensing information of the position sensor, and obtain contact position information of the object based on the sensing information; and a communicator configured to transmit the contact position information to the bio-information measuring apparatus.

The position sensor may include electrode parts disposed on at least two positions around the guide groove.

The processor may obtain the contact position information based on at least one from among an impedance and a capacitance measured at the electrode parts when the object comes into contact with the pulse wave sensor.

BRIEF DESCRIPTION OF THE DRAWINGS

These and/or other aspects of the disclosure will become apparent and more readily appreciated from the following description of the exemplary embodiments, taken in conjunction with the accompanying drawings.

DETAILED DESCRIPTION

Figure 1:
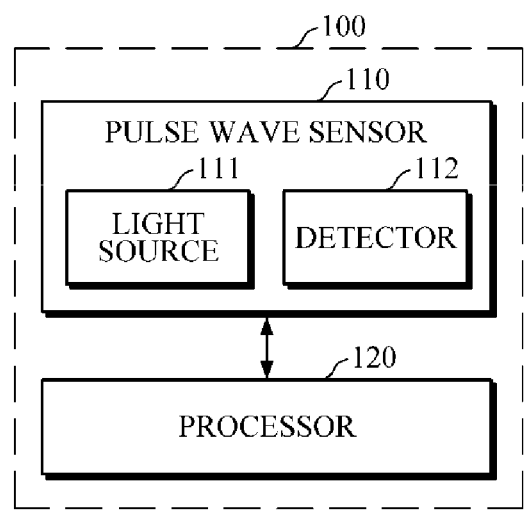
FIG. 1 is a block diagram illustrating an example of a bio-information measuring apparatus according to an exemplary embodiment.

Details of exemplary embodiments are provided in the following detailed description with reference to the accompanying drawings. The disclosure may be understood more readily by reference to the following detailed description of exemplary embodiments and the accompanying drawings. The disclosure may, however, be embodied in many different forms and should not be construed as being limited to the embodiments set forth herein. Rather, these embodiments are provided so that the disclosure will be thorough and complete and will fully convey the concept of the invention to those skilled in the art, and the disclosure will only be defined by the appended claims Like reference numerals refer to like elements throughout the specification.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as or 'module', etc., should be understood as a unit that performs at least one function or operation and that may be embodied as hardware, software, or a combination thereof.

Hereinafter, embodiments of a bio-information measuring apparatus and bio-information measuring method will be described in detail with reference to the accompanying drawings.

FIG. 1 is a block diagram illustrating an example of a bio-information measuring apparatus according to an exemplary embodiment.

Referring to FIG. 1, a bio-information measuring apparatus 100 includes a pulse wave sensor 110 and a processor 120.

The pulse wave sensor 110 is a sensor which measures a pulse wave signal (e.g., photoplethysmography (PPG) signal) from an object. In an embodiment, the pulse wave sensor 110 may measure a multi-wavelength pulse wave signal from an object. In this case, the multiple wavelengths of the pulse wave signal may include an infrared wavelength, a red wavelength, a green wavelength, a blue wavelength, and the like.

The pulse wave sensor 110 may include a light source 111 which emits light onto an object, and a detector 112 which detects light emitted by the light source 111 and scattered or reflected from body tissues, such as the skin surface, blood vessels, and the like, of the object.

The light source 111 may include a light emitting diode (LED), a laser diode (LD), a fluorescent body (or fluorescent element), and the like. One or more light sources 111 may be provided to emit light of multiple wavelengths to detect a multi-wavelength pulse wave signal. For example, the pulse wave sensor 110 may include a plurality of light sources 111, each of which may emit light of different wavelengths. In another example, the pulse wave sensor 110 may include a single light source 111 which may sequentially emit light of different wavelengths under the control of the processor 120; or a single light source 111 which may emit light in a wide range of wavelengths including a range of multiple wavelengths desired to be detected.

The detector 112 may include one or more photo diodes, photo transistors (PTr), image sensors (e.g., CMOS image sensor), and the like. The detector 112 may be provided to correspond to each of the plurality of light sources 111 to detect light of multiple wavelengths. Alternatively, a plurality of detectors 112 may be provided to respond to light of different wavelengths to detect light of multiple wavelengths emitted by the single light source 111.

The processor 120 may drive the pulse wave sensor 110 in response to a request to measure bio-information. The processor 120 may sequentially drive one or more light sources 111 based on a predetermined light source driving condition so that the light sources 111 may emit light of multiple wavelengths. In this case, the light source driving condition may include conditions of a light intensity, a pulse duration, and the like of each light source 111. For example, the processor 120 may include a central processing unit (CPU).

Upon receiving, from the pulse wave sensor 110, a multi-wavelength pulse wave signal detected at a specific time, the processor 120 may extract a contact pressure signal corresponding to a contact pressure between an object and the pulse wave sensor 110 by analyzing the received multi-wavelength pulse wave signal.

Further, the processor 120 may determine a measurement state (or state of bio-information measurement) based on the extracted contact pressure signal. In response to the contact pressure between the object and the pulse wave sensor 110 being changed, a waveform of the detected pulse wave signal is also changed, such that the processor 120 may indicate to the object to increase or decrease a contact pressure for the pulse wave sensor based on the contact pressure corresponding to the extracted contact pressure signal.

For example, upon extracting a contact pressure signal at a specific time, the processor 120 may generate guide information which includes the actual contact pressure corresponding to the contact pressure signal at the specific time. Further, upon extracting the actual contact pressure at the specific time, the processor 120 may compare the actual contact pressure with a reference pressure, and may generate guide information, which may include warning information, based on a result of the comparison. In this case, the reference pressure may be determined to be a peak value, a lowest value, a normal pressure range, and the like. In the case where the actual contact pressure exceeds the peak value, is below the lowest value, or is outside the normal pressure range, the processor 120 may generate warning information indicating that the contact pressure is not in a normal range. For example, the normal range may be within a certain threshold difference from the reference pressure.

Figure 2:
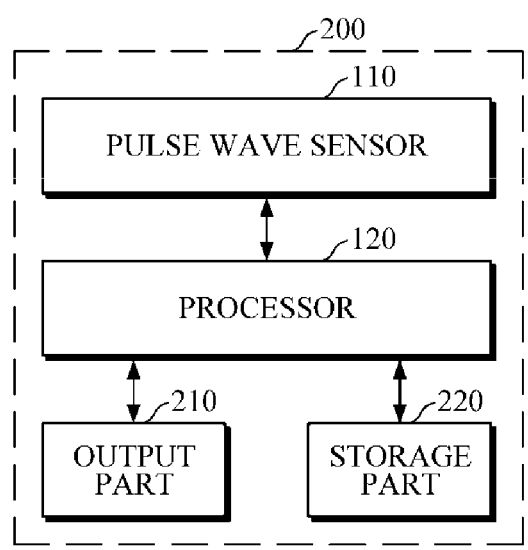
FIG. 2 is a block diagram illustrating another example of a bio-information measuring apparatus according to an exemplary embodiment.

The processor 120 may measure No-information based on the received multi-wavelength pulse wave signal and/or the contact pressure signal. In this case, the bio-information may include systolic blood pressure, diastolic blood pressure, vascular age, degree of arteriosclerosis, aortic pressure waveform, vascular compliance, stress index, degree of fatigue, and the like, but is not limited thereto. FIG. 2 is a block diagram illustrating another example of a bio-information measuring apparatus according to an exemplary embodiment.

Referring to FIG. 2, the bio-information measuring apparatus 200 includes a pulse wave sensor 110, a processor 120, an output part (or output device) 210, and a storage part (or storage device) 220. The pulse wave sensor 110 and the processor 120 are described above with reference to FIG. 1, such that description below will be made based on other parts.

The output part 210 may output the multi-wavelength pulse wave signal detected by the pulse wave sensor 110 or a processing result, e.g., a measurement result of bio-information, of the processor 120. The output part 210 may include a speaker, a printer, a display, or any other output device.

In an embodiment, the output part 210 may visually provide various types of information to a user on display. Alternatively, the output part 210 may provide a user with various types of information in a non-visual manner such as voice, vibration, tactility, and the like, by using a speaker module (e.g., speaker), a haptic module (e.g., vibrator or vibration motor), or the like. For example, in the case where a measured blood pressure value falls outside a normal range, the output part 210 may provide warning by displaying the blood pressure in red, or may provide additional warning information through vibration or tactility by using a haptic module.

Further, upon receiving a request for measuring bio-information, the output part 210 may output guide information regarding a measurement state of a multi-wavelength pulse wave signal under the control of the processor 120. In this case, the guide information may include information on the reference pressure to be applied by an object to the pulse wave sensor 110 while the pulse wave sensor 110 detects a pulse wave signal, and/or the actual contact pressure extracted by the processor 120.

For example, upon receiving a request for measuring bio-information, the output part 210 may visually display, on a display screen, the extracted actual contact pressure at each time alone or along with the reference pressure under the control of the processor 120. Alternatively, the output part 210 may visually display warning information, which is generated by comparing, by the processor 120, the reference pressure with the extracted actual contact pressure; or may output the warning information in voice, vibration, and the like.

The storage part 220 may store various types of reference information or a processing result of the pulse wave sensor 110 and the processor 120. In this case, various types of reference information may include user information, such as a user's age, gender, health state, and the like, guide information regarding the aforementioned measurement state, or information for use in measuring bio-information, such as a bio-information measurement model and the like.

In this case, the storage part 250 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Figure 3:
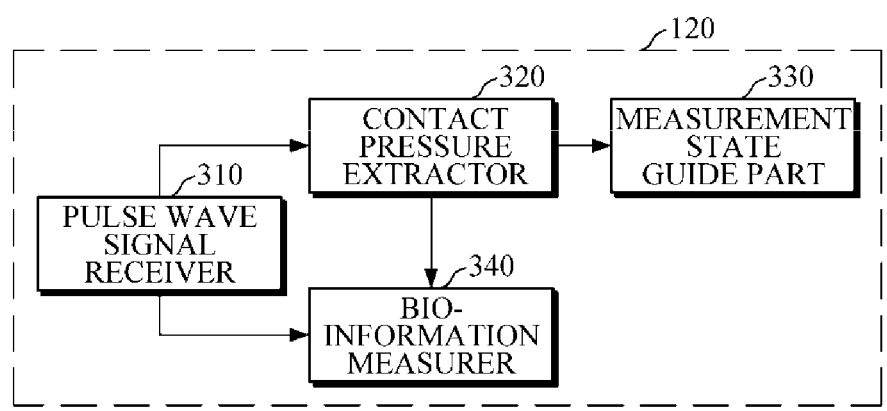
FIG. 3 is a block diagram illustrating an example of a configuration of a processor of a bio-information measuring apparatus according to an exemplary embodiment.

FIG. 3 is a block diagram illustrating an example of a configuration of a processor of a bio-information measuring apparatus according to an exemplary embodiment. FIGS. 4A to 4E are diagrams explaining a method of extracting a contact pressure by using a multi-wavelength pulse wave signal according to an exemplary embodiment. Referring to FIGS. 3 to 4E, the configuration of the processor 120 of FIGS. 1 and 2 will be described in further detail.

Referring to FIG. 3, the processor 120 of a bio-information measuring apparatus according to an exemplary embodiment includes a pulse wave signal receiver 310, a contact pressure extractor 320, a measurement state guide part 330, and a bio-information measurer 340.

The pulse wave signal receiver 310 may receive the detected multi-wavelength pulse wave signal from the pulse wave sensor 110, and may transmit the received multi-wavelength pulse wave signal to the contact pressure extractor 320 and the bio-information measurer 340. In this case, the pulse wave signal receiver 310 may be electrically connected with the pulse wave sensor 110.

Upon receiving the multi-wavelength pulse wave signal at a specific time from the pulse wave sensor 110, the contact pressure extractor 320 may extract a contact pressure between an object and the pulse wave sensor 110 at the specific time by analyzing the received multi-wavelength pulse wave signal.

Figure 4A:
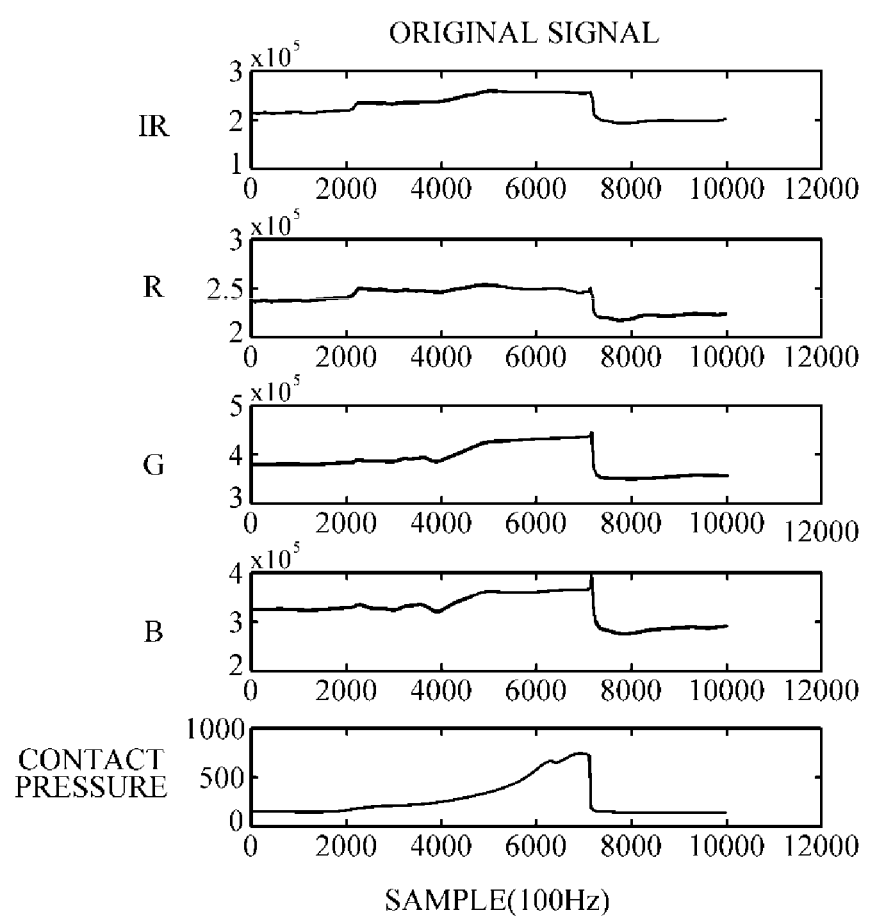
FIGS. 4A to 4E are diagrams explaining a method of extracting a contact pressure by using a multi-wavelength pulse wave signal according to an exemplary embodiment.
Figure 4B:
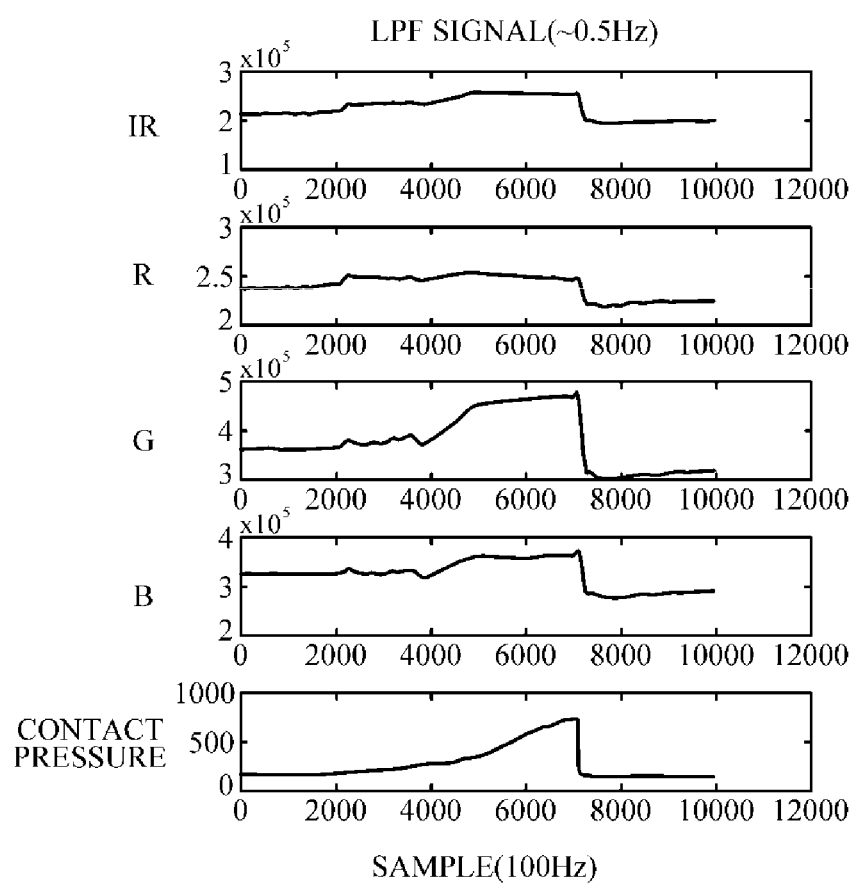
Figure 4C:
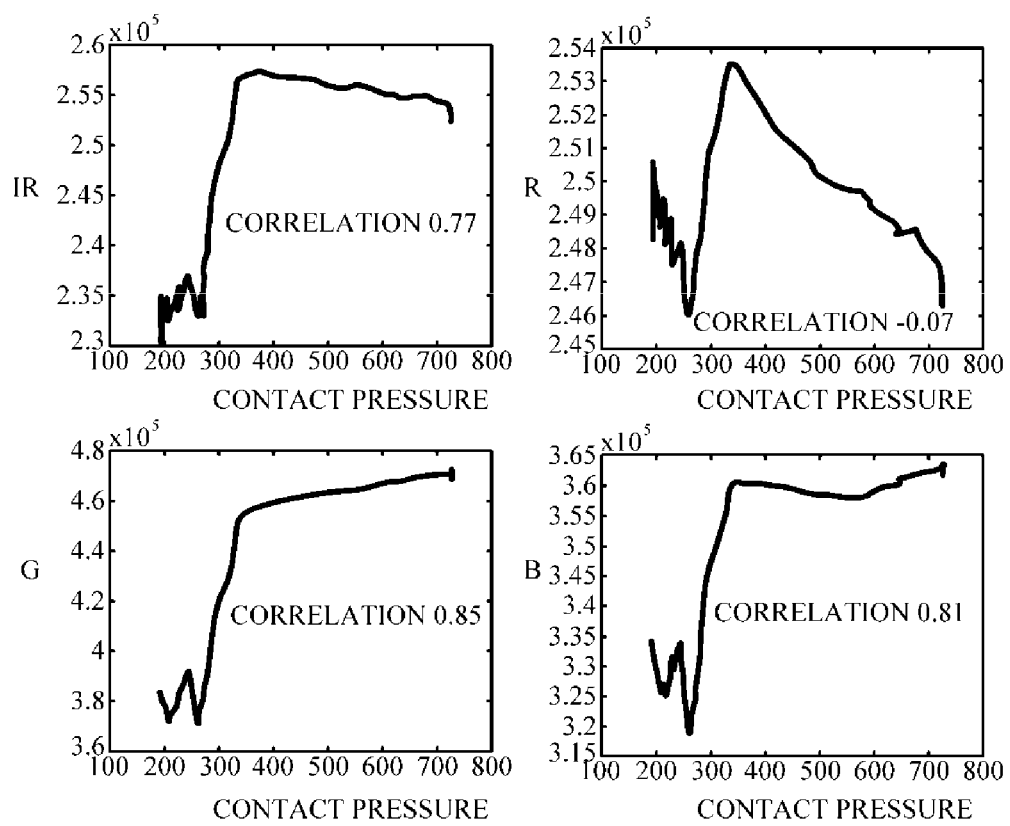

For example, FIGS. 4A to 4C are diagrams explaining a correlation between a pulse wave signal of each wavelength and a contact pressure, and the contact pressure extractor 320 may extract the contact pressure by using such correlation between a multi-wavelength pulse wave signal and a contact pressure.

FIG. 4A illustrates pulse wave signals of an infrared (IR) wavelength, a red (R) wavelength, a green (G) wavelength, and a blue (B) wavelength which are detected from a sample for a predetermined period of time; and an actual contact pressure applied to the pulse wave sensor for the predetermined period of time. FIG. 4B illustrates pulse wave DC signals of the wavelengths IR, R, G, and B which are obtained by passing the pulse wave signals of the wavelengths IR, R, G, and B through a Low Pass Filter (LPF); and an actual contact pressure applied to the pulse wave sensor. FIG. 4C illustrates a correlation between a contact pressure and pulse wave DC signals of the wavelengths IR, R, G, and B, which are extracted from the pulse wave DC signals of the wavelengths IR, R, G, and B obtained in FIG. 4B in a section where the contact pressure is increased. As illustrated therein, it can be seen that except for the pulse wave DC signal of the red (R) wavelength, there is a high correlation between the pulse wave DC signals of other wavelengths IR, G, and B and the contact pressure.

Upon receiving the multi-wavelength pulse wave signal, the contact pressure extractor 320 may generate a pulse wave DC signal of each wavelength by passing the multi-wavelength pulse wave signal through the Low Pass Filter (LPF), as described above. Further, the contact pressure extractor 320 may extract a contact pressure signal by combining the generated two or more pulse wave DC signals of each wavelength.

For example, the contact pressure extractor 320 may generate differential signals by differentiating the pulse wave DC signal of the blue (B) wavelength obtained at a specific time from the pulse wave DC signals of other wavelengths IR, R, and G, and may extract a contact pressure at the specific time by combining the generated differential signals. For example, the contact pressure extractor 320 may obtain a ratio of two differential signals as shown in the following Equation 1, and may use the ratio as a contact pressure at the specific time; or may extract a contact pressure by applying the ratio to a pre-defined correlation model. In this case, the correlation model may be defined by an algorithm with a mathematical function or in the form of a matching table, which may represent a correlation between a ratio of two differential signals and the contact pressure.

$$Dr=(Sg-Sb)/(Sr-Sb) \quad CP=a \times Dr+b \qquad \text{[Equation 1]}$$

Herein, Sg denotes a pulse wave DC signal of the green (G) wavelength, Sb is a pulse wave DC signal of the blue (B) wavelength, Sr denotes a pulse wave DC signal of the red (R) wavelength, and Dr denotes a ratio between differential signals. Further, DC denotes a contact pressure, and a and b denote any constants defining a correlation between a ratio of differential signals and a contact pressure.

In conventional PPG-based cuffless blood pressure measuring methods, there are problems in that PPG measurement is influenced by a contact pressure between the object and the pulse wave sensor because a change in the contact pressure between the object and the pulse wave sensor affects a shape of a PPG waveform. Therefore, the accuracy of estimating the blood pressure is degraded. In contrast, solutions according to an exemplary embodiment can solve these problems by obtaining a correlation between a pulse wave signal of each wavelength and the contact pressure by using a ratio between difference signals of the multi-wavelength pulse wave signal. Therefore, bio-info such as blood pressure be accurately measured without being influenced by contact pressure between the object and the pulse wave sensor. Also, according to an exemplary embodiment, accurate bio-information measurement can be performed even without using a pressure sensor.

Figure 4D:
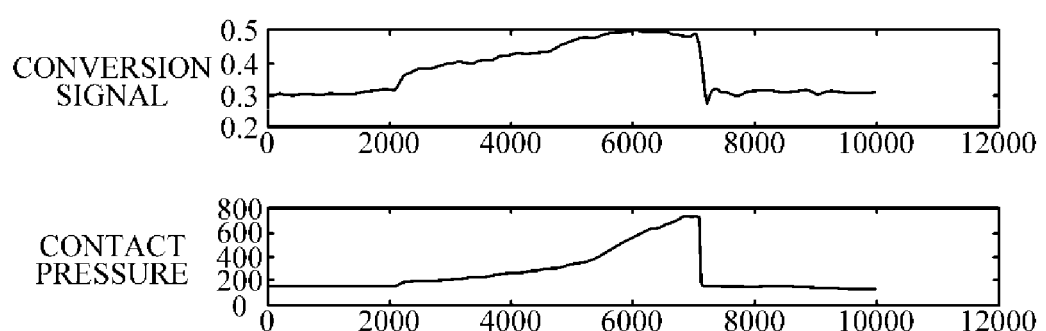
Figure 4E:
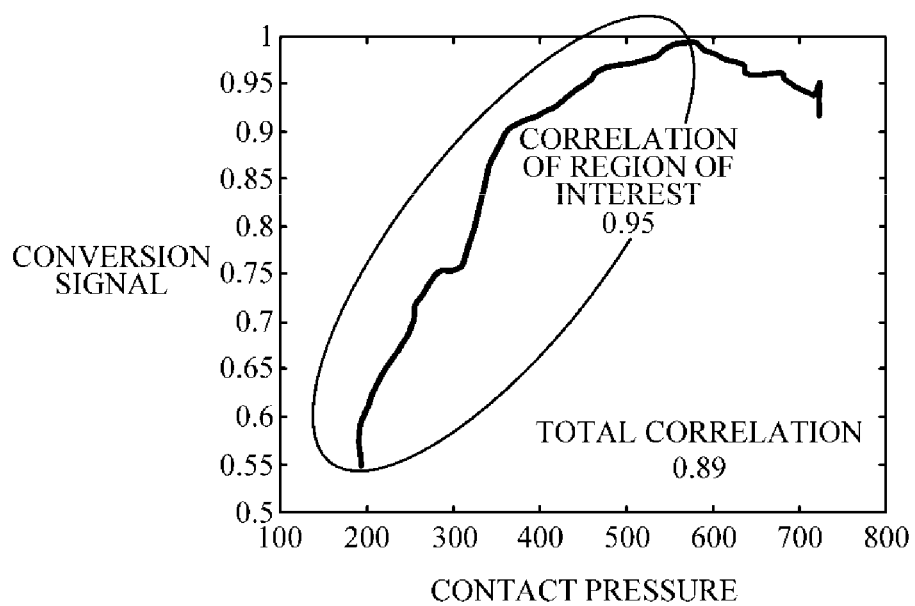

FIG. 4D illustrates a conversion signal generated based on a ratio of differential signals between multi-wavelength pulse wave DC signals during a predetermined period of time; and a contact pressure signal applied in practice by a user during a predetermined period of time. FIG. 4E illustrates a correlation between the conversion signal and the contact pressure. As illustrated in FIG. 4E, it can be seen that an overall correlation between the conversion signal and the contact pressure signal is 0.89; and there is a very high correlation of 0.95 between a conversion signal and a contact pressure signal in the section where a contact pressure is increased (or a region of interest).

Once the contact pressure at a specific time is extracted as described above, the measurement state guide part 330 may determine a measurement state based on the extracted contact pressure, and may indicate a current measurement state based on the determination.

For example, once the contact pressure at a specific time is extracted, the measurement state guide part 330 may generate guide information which includes the extracted contact pressure and/or the reference pressure at the specific time. Alternatively, the measurement state guide part 330 may determine whether a measurement state is normal by comparing the extracted contact pressure at the specific time with the reference time at the specific time; and upon determining that the measurement state is not normal, the measurement state guide part 330 may generate warning information indicating that the measurement state is not normal. In addition, the measurement state guide part 330 may generate guide information which includes information regarding a degree of contact pressure that is desired to be increased or decreased by a user.

Upon generating the guide information, the measurement state guide part 330 may control the output part 210 to output the generated guide information to a user.

Once the pulse wave sensor 110 completes detection of a multi-wavelength pulse wave signal, the bio-information measurer 340 may measure bio-information by using the detected multi-wavelength pulse wave signal. In this case, the bio-information measurer 340 may measure bio-information by also considering a contact pressure during the time when the pulse wave signal is detected.

For example, the bio-information measurer 340 may measure blood pressure based on any one pulse wave signal among the multi-wavelength pulse wave signals, for example, a pulse wave signal of the infrared (IR) wavelength and the contact pressure. In this case, the bio-information measurer 340 may extract, as feature points, a pulse wave value or a contact pressure at a maximum peak point of the pulse wave signal, and may measure blood pressure based on the extracted feature points and a pre-defined measurement model. For example, the blood pressure measurement model may be defined by a mathematical algorithm.

In another example, the bio-information measurer 340 may measure blood pressure by using two or more of the multi-wavelength pulse wave signals, for example, pulse wave signals of the infrared (IR) and green (G) wavelengths. In this case, the bio-information measurer 340 may extract various feature points based on pulse wave signals in the section where the contact pressure is increased or decreased among the entire sections of two or more pulse wave signals, and may measure blood pressure by using the extracted feature points.

Figure 5:
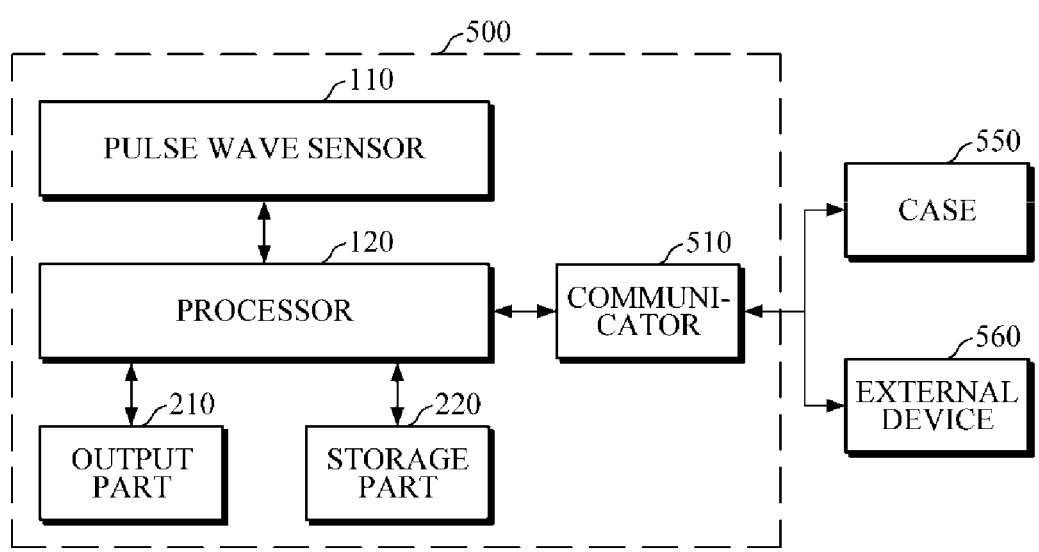
FIG. 5 is a block diagram illustrating yet another example of a bio-information measuring apparatus according to an exemplary embodiment.

FIG. 5 is a block diagram illustrating yet another example of a bio-information measuring apparatus according to an exemplary embodiment.

Referring to FIG. 5, a bio-information measuring apparatus 500 includes a pulse wave sensor 110, a processor 120, an output part 210, a storage part 220, and a communicator 510. The pulse wave sensor 110, the processor 120, the output part 210, and the storage part 220 may be the same or similar to those described above with reference to FIGS. 1 and 2, and repetitive descriptions will be avoided.

The communicator 510 may perform wired or wireless communication with a case (or case apparatus) 550 of a bio-information measuring apparatus 500 or various other external devices 250 under the control of the processor 120. In this case, the communicator 510 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

For example, in the case where the bio-information measuring apparatus 500 is accommodated in the case 550 of the bio-information measuring apparatus 500, the communicator 510 may communicate with the case 550, and may receive information regarding a contact position of an object (or contact position information) when the object contacts the pulse wave sensor 110. For example, the contact position information may indicate the contact position of the object with respect to the pulse wave sensor 110. In this case, the case 550 may include the above-described wireless communication module to communicate with the communicator 510. Further, the case 550 may include a connector for connection to a cable connector of the bio-information measuring apparatus 500, e.g., a USB port and the like, and may transmit and receive data through wired communication.

In another example, the communicator 510 may transmit, to the external device 560, a measurement result of pulse waves, an extraction result of contact pressure, a processing result of the processor 120, and the like, so that the external device 560 may, for example, manage a bio-information history of a user, may monitor a health state of a user, may output the bio-information history and a monitoring result of the health state, and the like. In this case, the external device 560 may include a smartphone, a tablet PC, a desktop computer, a laptop computer, medical equipment, and the like, but is not limited thereto. In another example, the communicator 510 may receive a bio-information measurement model to be used in measuring bio-information, reference information for calibration of bio-information, for example, cuff pressure, cuff blood pressure, and the like.

Upon receiving a request for measuring bio-information, the processor 120 may control the communicator 510 to be connected with the case 550 through communication, and may transmit a request for contact position information of an object to the case 550.

Upon receiving the contact position information of the object from the case 550, the processor 120 may generate guide information regarding a measurement state based on the received contact position information. In this case, the processor 120 may extract a contact pressure signal based on a multi-wavelength pulse wave signal, and may generate guide information based on the extracted contact pressure signal, and the contact position information.

For example, the processor 120 may determine whether an object is in normal contact with the pulse wave sensor 110 by comparing a contact position between the object and the pulse wave sensor 110 with a reference position based on the received contact position information; and in response to determination that a state of contact (or contact state) between the object and the pulse wave sensor 110 is not normal, the processor 120 may generate warning information. For example, the reference position may include at least one position on the pulse wave sensor 110. Further, the processor 120 may generate a guide image, e.g., an image which is obtained by superposing an image of the object on an image of the pulse wave sensor, based on the contact position information. In the case where the object is outside a normal contact position (or outside a normal range of the contact position), the processor 120 may display an identification mark, which indicates a moving direction of the object, by superposing the identification mark on the pulse wave sensor image. For example, the normal range of the contact position may be within a certain threshold difference from the reference position.

The output part 210 may output a processing result of the processor 120, for example, the generated guide information, a measurement result of bio-information, and the like, in various manners. For example, the output part 210 may visually output the result on a display screen or may output the result in voice through a voice signal. Alternatively, the output part 210 may output warning information through vibration or tactility by using a haptic module. In conventional PPG-based cuffless blood pressure measuring methods, there are problems in that PPG measurement is influenced by a contact position of the object when the object contacts the pulse wave sensor because the contact position of the object affects a shape of a PPG waveform. Therefore, the accuracy of estimating the blood pressure is degraded. In contrast, solutions according to an exemplary embodiment can solve these problems by determining whether the object is in a normal contact position or within a normal range of the contact position. Therefore, bio-information such as blood pressure can be accurately measured.

Figure 6:
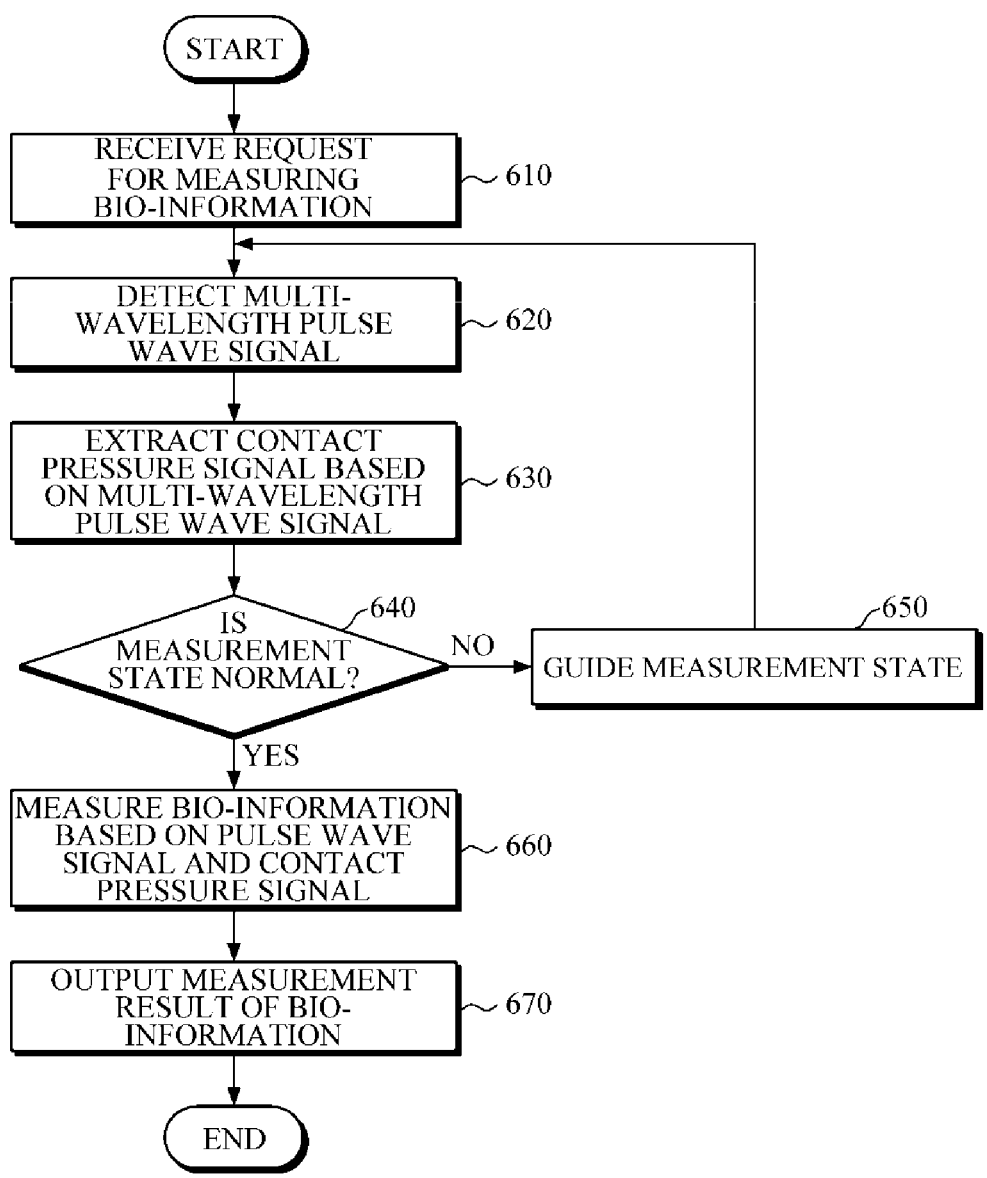
FIG. 6 is a flowchart illustrating an example of a bio-information measuring method according to an exemplary embodiment.

FIG. 6 is a flowchart illustrating an example of a bio-information measuring method according to an exemplary embodiment.

FIG. 6 may be an example of a bio-information measuring method performed by the bio-information measuring apparatuses 100 and 200 according to the embodiments of FIGS. 1 and 2.

Upon receiving a request for measuring bio-information in 610, the bio-information measuring apparatus may control the pulse wave sensor to detect a multi-wavelength pulse wave signal in 620. In this case, the multiple wavelengths include an infrared wavelength, a green wavelength, a red wavelength, a blue wavelength, and the like, but are not limited thereto. The pulse wave sensor may include one or more light sources to emit light of multiple wavelengths. For example, the pulse wave sensor may include a single light source configured to emit light in a range of multiple wavelengths, or a plurality of light sources configured to emit light of each of the multiple wavelengths. Further, the pulse wave sensor may include one or more detectors.

Then, upon detecting the multi-wavelength pulse wave signal in 620, the bio-information measuring apparatus may extract a contact pressure signal based on the detected multi-wavelength pulse wave signal in 630. For example, the bio-information measuring apparatus may generate a pulse wave DC signal of each wavelength by passing the multi-wavelength pulse wave signal through the Low Pass Filter (LPF), and may extract a contact pressure signal by combining the generated two or more pulse wave DC signals of each wavelength. In this case, based on the pulse wave DC signal of the blue wavelength, the bio-information measuring apparatus may generate differential signals by differentiating the pulse wave DC signal of the blue wavelength from the pulse wave DC signals of other wavelengths, and may extract a contact pressure based on a ratio of the generated differential signals.

Subsequently, the bio-information measuring apparatus may determine whether a measurement state of a pulse wave signal is normal based on the extracted contact pressure in 640. In response to the contact pressure between the object and the pulse wave sensor being changed, a waveform of the detected pulse wave signal is also changed. Accordingly, in order to improve reproducibility of the detected pulse wave signal, maintaining a contact pressure to be constant is desirable. Thus, the bio-information measuring apparatus may determine whether the measurement state is normal by comparing the extracted contact pressure with the reference pressure.

Next, upon determination in 640 that the measurement state is not normal, the bio-information measuring apparatus may guide (or indicate or output) a measurement state in 650. The bio-information measuring apparatus may generate information regarding the extracted contact pressure or the reference pressure, warning information indicating that the contact pressure is not a normal pressure, information regarding a degree of contact pressure desired to be increased or decreased by a user, and the like, and may provide the generated information to a user, thereby guiding the user to maintain a contact pressure corresponding to the reference pressure.

Then, upon determination in 640 that the measurement state is normal, the bio-information measuring apparatus may measure bio-information based on the detected multi-wavelength pulse wave signal and/or the contact pressure signal in 660. For example, the bio-information measuring apparatus may measure blood pressure based on one of the multi-wavelength pulse wave signals, and the contact pressure. Alternatively, the bio-information measuring apparatus may measure blood pressure by using two or more of the multi-wavelength pulse wave signals. In this case, the bio-information measuring apparatus may extract feature points based on the pulse wave signal and the contact pressure signal, and may measure blood pressure by combining the extracted feature points.

Subsequently, the bio-information measuring apparatus may output a measurement result of bio-information in 670. For example, the bio-information measuring apparatus may visually provide a measurement result of bio-information, the extracted contact pressure, and the like to a user on a display. Alternatively, the bio-information measuring apparatus may provide a user with warning information in a non-visual manner such as voice, vibration, tactility, and the like, by using a speaker module, a haptic module, or the like.

Figure 7:
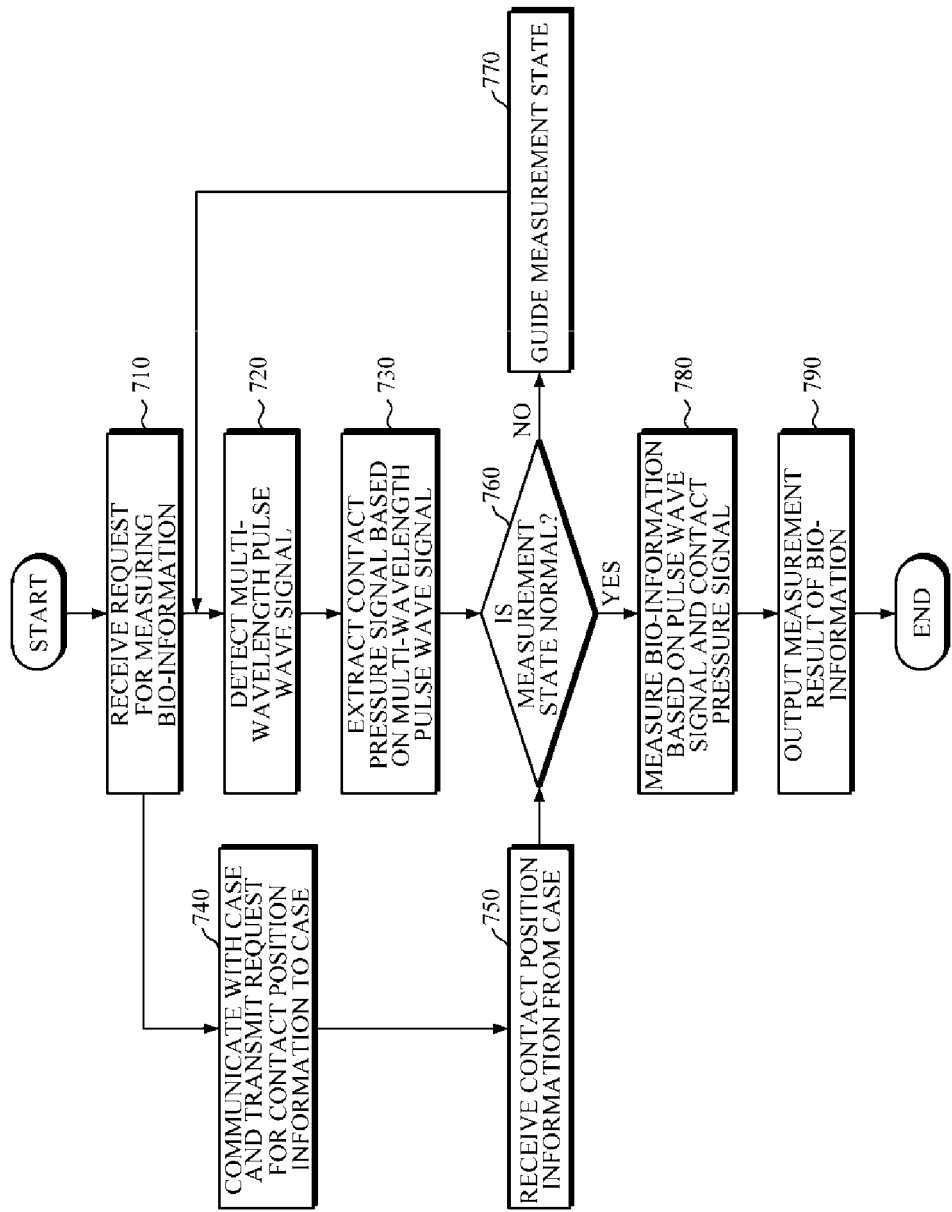
FIG. 7 is a flowchart illustrating another example of a bio-information measuring method according to an exemplary embodiment.

FIG. 7 is a flowchart illustrating another example of a bio-information measuring method according to an exemplary embodiment.

FIG. 7 may be an example of a bio-information measuring method performed by the bio-information measuring apparatus 500 according to the embodiment of FIG. 5.

Upon receiving a request for measuring bio-information in 710, the bio-information measuring apparatus may control the pulse wave sensor to detect a multi-wavelength pulse wave signal in 720. In this case, the multiple wavelengths include an infrared wavelength, a green wavelength, a red wavelength, a blue wavelength, and the like, but are not limited thereto.

Then, upon detecting the multi-wavelength pulse wave signal in 720, the bio-information measuring apparatus may extract a contact pressure signal based on the detected multi-wavelength pulse wave signal in 730. In this case, as described above, the bio-information measuring apparatus may generate a pulse wave DC signal of each wavelength by passing the pulse wave signal of each wavelength through the Low Pass Filter (LPF), and may extract a contact pressure signal based on a combination of differential signals which are obtained by differentiating the pulse wave DC signal of the blue wavelength from the pulse wave DC signals of other wavelengths.

Upon receiving a request for measuring bio-information in 710, the bio-information measuring apparatus may be connected with the case thereof through wired or wireless communication, and may transmit a request for information on a contact position between an object and the pulse wave sensor to the case of the bio-information measuring apparatus in 740.

Subsequently, the bio-information measuring apparatus may receive the information on the contact position of the object from the case thereof in 750.

Next, the bio-information measuring apparatus may determine whether a measurement state of the pulse wave signal is normal based on the extracted contact pressure and/or the contact position information in 760. In the case where the contact position between the object and the pulse wave sensor is changed, it may be difficult to detect the pulse wave signal with improved reproducibility. Accordingly, the bio-information measuring apparatus may determine whether an actual contact position is normal by comparing the extracted contact position with the reference position.

Then, upon determination in 760 that a measurement state is not normal, the bio-information measuring apparatus may guide (or indicate or output) a measurement state in 770. For example, the bio-information measuring apparatus may generate guide information regarding a current measurement state, and may output the generated guide information to a display and the like. In this case, the guide information may include the extracted actual contact pressure, the reference pressure, warning information indicating that the contact pressure is not a normal pressure, information regarding a degree of contact pressure desired to be increased or decreased by a user, warning information indicating that a current contact position is not normal, a guide image which is obtained by superposing, on an image of the pulse wave sensor, an image of the object or an identification mark for guiding a normal position, and the like.

Next, upon determination in 760 that the measurement state is normal, the bio-information measuring apparatus may measure bio-information based on the detected multi-wavelength pulse wave signal and/or the contact pressure signal in 780.

Then, the bio-information measuring apparatus according to an exemplary embodiment may output a measurement result of bio-information to a user in 790.

Figure 8A:
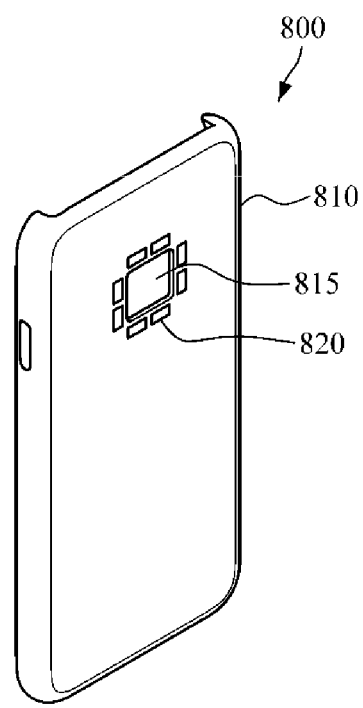
FIG. 8A is a diagram illustrating an example of a case apparatus of a bio-information measuring apparatus according to an exemplary embodiment.
Figure 8B:
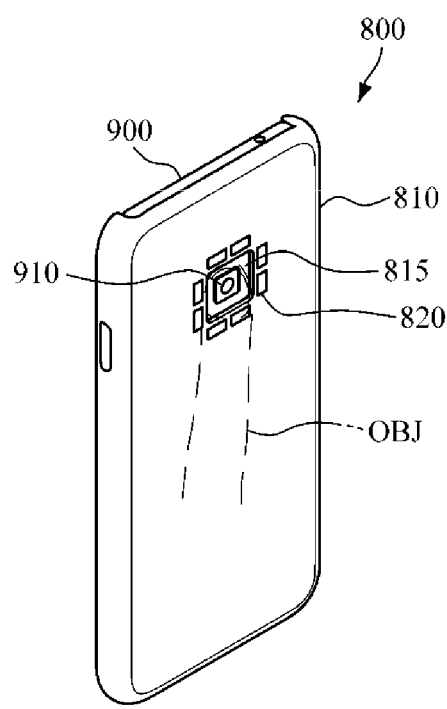
FIG. 8B is a diagram illustrating connection of a bio-information measuring apparatus with a case apparatus according to an exemplary embodiment.
Figure 8C:
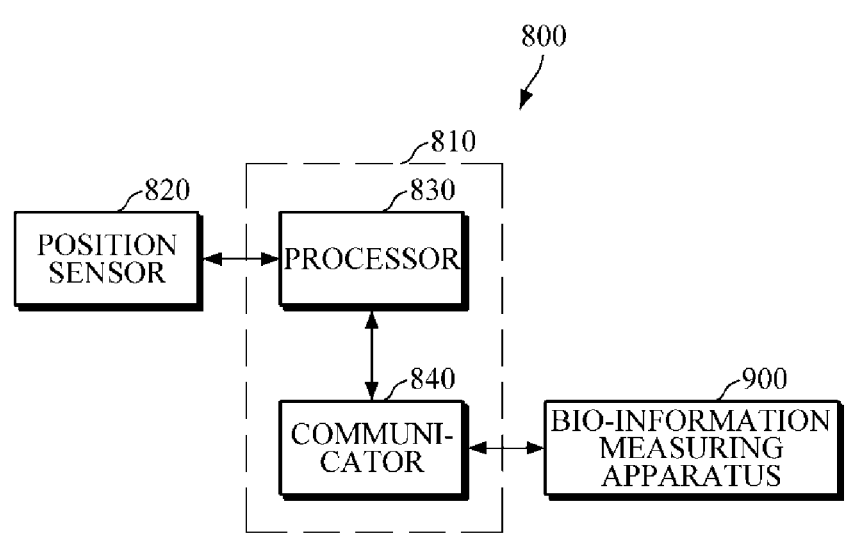
FIG. 8C is a block diagram illustrating an example of a case apparatus for a bio-information measuring apparatus according to an exemplary embodiment.

FIG. 8A is a diagram illustrating an example of a case of a bio-information measuring apparatus according to an exemplary embodiment. FIG. 8B is a diagram illustrating connection of a bio-information measuring apparatus with a case thereof according to an exemplary embodiment. FIG. 8C is a block diagram illustrating an example of a case of a bio-information measuring apparatus according to an exemplary embodiment.

Referring to FIGS. 8A and 8B, a case (or case apparatus) 800 of a bio-information measuring apparatus may include a main body 810 to accommodate a bio-information measuring apparatus 900. As illustrated therein, the main body 810 may include an accommodation space at a front surface thereof to accommodate a rear surface of the bio-information measuring apparatus 900 while covering the sides of the bio-information measuring apparatus 900. However, the main body 810 of the case 800 is not limited thereto, and may be modified according to various shapes of the bio-information measuring apparatus 900.

A guide groove 815 may be provided on a rear surface of the main body 810 to expose a pulse wave sensor 910 of the bio-information measuring apparatus 900 to the outside. The guide groove 815 may guide an object OBJ to accurately contact the pulse wave sensor 910 when bio-information is measured. The main body 810 may be provided to have a predetermined thickness so that the pulse wave sensor 910 does not protrude to the outside of the guide groove 815. For example, the object OBJ may be a finger of a user.

Position sensors 820 may be disposed around the guide groove 815 provided on the main body 810. The position sensors 820 may be disposed on a rear surface of the main body 810 around the guide groove 815 or on inner edges of the guide groove 815.

When the object OBJ comes into contact with the pulse wave sensor 910, the position sensor 820 may sense a contact position of the object OBJ. In this case, the position sensor 820 may include an electrode part capable of measuring an impedance or a capacitance. The electrode part may be disposed at two opposing positions around the guide groove 815. For example, the electrode part may be disposed on the top/bottom portions of the guide groove 815. Alternatively, the electrode part may be disposed on the left/right portions of the guide groove 815. Further, the electrode part may also be disposed on any one of top/bottom/left/right portions of the guide groove 815.

Referring to FIG. 8C, the case 800 may include a processor 830 and a communicator 840 provided in the main body 810.

Upon receiving a request for contact position information of the object from the bio-information measuring apparatus 900 through the communicator 840, the processor 830 may control the position sensors 820 to obtain position information of the object currently in contact with the pulse wave sensor 910.

For example, in the case where the position sensor 820 includes at least two electrode parts disposed on at least two opposing positions of the guide groove 815 to measure an impedance, the processor 830 may supply a current to each electrode part, and may measure an impedance of each electrode part by measuring a voltage of each electrode part.

In another example, in the case where the position sensor 820 includes at least two electrode parts disposed on at least two opposing positions of the guide groove 815 to measure a capacitance, the processor 830 may supply a current to each electrode part, and may obtain contact position information from a capacitance accumulated in each electrode part.

The processor 830 may compare impedances of each electrode part or accumulated capacitances thereof, which are calculated through each electrode part, and may obtain contact position information indicating whether the object is positioned exactly on the center of the guide groove 815 or whether object leans to one side while in contact therewith.

The main body 810 may include a battery to supply power to the bio-information measuring apparatus 900. In this case, the processor 830 may supply a current to the electrode part of the position sensor 820 by using power of the mounted battery. However, the embodiment is not intended to be limiting, and the battery may not be separately mounted in the main body 810, in which case the processor 830 may supply a current to the position sensor 820 by using power of the bio-information measuring apparatus 900.

In conventional PPG-based cuffless blood pressure measuring methods, there are problems in that PPG measurement is influenced by a contact position of the object when the object contacts the pulse wave sensor because the contact position of the object affects a shape of a PPG waveform. Therefore, the accuracy of estimating the blood pressure is degraded. In contrast, solutions according to an exemplary embodiment can solve these problems by arranging position sensors around the guide groove 815 provided on the main body 810 to expose the pulse wave sensor 910 of the bio-information measuring apparatus 900 to the outside, accurate contact position can be achieved. Therefore, bio-information such as blood pressure can be accurately measured.

The communicator 840 may perform wired and wireless communication with the bio-information measuring apparatus 900. Upon receiving a request for contact position information of the object from the bio-information measuring apparatus 900, the communicator 840 may transmit the request to the processor 830, and may transmit the contact position information to the bio-information measuring apparatus 900 under the control of the processor 830.

The exemplary embodiments may be implemented in a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments according to the exemplary embodiments may be easily deduced by one of ordinary skill in the art.

At least one of the components, elements, modules or units represented by a block as illustrated in the drawings may be embodied as various numbers of hardware, software and/or firmware structures that execute respective functions described above, according to an exemplary embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the above block diagrams, communication between the components, elements or units may be performed through the bus. Functional aspects of the above exemplary embodiments may be implemented in algorithms that execute on one or more processors. Furthermore, the components, elements or units represented by a block or processing steps may employ any number of related art techniques for electronics configuration, signal processing and/or control, data processing and the like.

Although a few embodiments have been shown and described, it would be appreciated by those skilled in the art that changes may be made in the example embodiments without departing from the principles and spirit of the disclosure, the scope of which is defined in the claims and their equivalents.

What is claimed is:

1. An apparatus for measuring bio-information, the apparatus comprising:
   a pulse wave sensor configured to emit light having a plurality of wavelengths onto an object, and to detect a multi-wavelength pulse wave signal from the object; and
   a processor configured to obtain a differential signal between detected multi-wavelength pulse wave signals, obtain a contact pressure signal based on the differential signal, the contact pressure signal indicating a pressure between the object and the pulse wave sensor, and to generate information regarding a measurement state of the object based on the contact pressure signal.

2. The apparatus of claim 1, wherein the pulse wave sensor comprises:
   one or more light sources configured to emit the light having the plurality of wavelengths onto the object; and
   one or more detectors configured to detect the multi-wavelength pulse wave signal from the object.

3. The apparatus of claim 2, wherein the one or more light sources comprise at least one from among a light emitting diode (LED), a laser diode (LD), and a fluorescent element.

4. The apparatus of claim 1, wherein the plurality of wavelengths comprise two or more from among an infrared wavelength, a red wavelength, a green wavelength, and a blue wavelength.

5. The apparatus of claim 4, wherein the processor is further configured to obtain the differential signal between a pulse wave signal having the blue wavelength and pulse wave signals having other wavelengths among the plurality of wavelengths.

6. The apparatus of claim 5, wherein the processor is further configured to obtain the contact pressure signal based on a ratio of a first differential signal, which is obtained by differentiating the pulse wave signal having the blue wavelength from a pulse wave signal having the green wavelength, and a second differential signal which is obtained by differentiating the pulse wave signal having the blue wavelength from a pulse wave signal having the red wavelength.

7. The apparatus of claim 1, wherein the processor is further configured to, based on a determination that the pressure between the object and the pulse wave sensor, indicated by the contact pressure signal, is not within a threshold difference from a reference pressure, generate information regarding the pressure between the object and the pulse wave sensor.

8. The apparatus of claim 7, further comprising an output part configured to output, under control by the processor, generated information regarding the pressure between the object and the pulse wave sensor.

9. The apparatus of claim 1, wherein the processor is further configured to measure bio-information based on the multi-wavelength pulse wave signal and the contact pressure signal.

10. The apparatus of claim 9, wherein the processor is further configured to obtain a feature point based on the multi-wavelength pulse wave signal and the contact pressure signal, and measure the bio-information by using the feature point and a measurement model.

11. The apparatus of claim 9, wherein the bio-information comprises one or more from among blood pressure, vascular age, degree of arteriosclerosis, aortic pressure waveform, vascular compliance, and stress index.

12. A method of measuring bio-information, the method comprising:
    emitting light having a plurality of wavelengths onto an object;
    detecting a multi-wavelength pulse wave signal from the object;
    obtaining a differential signal between detected multi-wavelength pulse wave signals;
    obtaining a contact pressure signal based on the differential signal, the contact pressure signal indicating a pressure between the object and a pulse wave sensor; and
    generating information regarding a measurement state of the object based on the contact pressure signal.

13. The method of claim 12, wherein the plurality of wavelengths comprise two or more from among an infrared wavelength, a red wavelength, a green wavelength, and a blue wavelength.

14. The method of claim 13, wherein the obtaining the differential signal comprises obtaining the differential signal between a pulse wave signal having the blue wavelength and pulse wave signals of other wavelengths among the plurality of wavelengths.

15. The method of claim 14, wherein the obtaining the contact pressure signal based on the differential signal comprises obtaining the contact pressure signal based on a ratio of a first differential signal, which is obtained by differentiating the pulse wave signal having the blue wavelength from a pulse wave signal having the green wavelength, and a second differential signal which is obtained by differentiating the pulse wave signal having the blue wavelength from a pulse wave signal having the red wavelength.

16. The method of claim 12, wherein the generating information regarding the pressure comprises:
    based on a determination that the pressure between the object and the pulse wave sensor, indicated by the contact pressure signal, is not within a threshold difference from a reference pressure, generating information regarding the pressure between the object and the pulse wave sensor.

17. The method of claim 16, further comprising outputting generated information regarding the pressure between the object and the pulse wave sensor.

18. The method of claim 12, further comprising measuring bio-information based on the multi-wavelength pulse wave signal and the contact pressure signal.

19. A bio-information measuring apparatus, comprising:
    a pulse wave sensor configured to emit light having a plurality of wavelengths onto an object, which is in contact with the pulse wave sensor, and to detect a multi-wavelength pulse wave signal from the object;
    a communicator circuit configured to communicate with a case apparatus, which is configured to accommodate the bio-information measuring apparatus, and to receive contact position information of the object from the case apparatus, the contact position information indicating a contact position of the object with respect to the pulse wave sensor; and
    a processor configured to generate a measurement state of the object based on the contact position information,
    wherein the processor is further configured to compare the contact position information received from the case apparatus with reference position information and, in response to determining that the contact position of the object with respect to the pulse wave sensor is not within a threshold difference from a reference position, generate information on the contact position.

20. The apparatus of claim 19, further comprising an output part configured to output generated information on the contact position.

21. The apparatus of claim 19, wherein the processor is further configured to obtain a contact pressure signal based on the multi-wavelength pulse wave signal, the contact pressure signal indicating a pressure between the object and the pulse wave sensor, and generate the measurement state further based on the contact pressure signal.

22. The apparatus of claim 21, wherein
    the plurality of wavelengths comprise two or more from among an infrared wavelength, a red wavelength, a green wavelength, and a blue wavelength, and
    the processor is further configured to obtain the contact pressure signal by using a differential signal obtained by differentiating a pulse wave signal having the blue wavelength, among detected multi-wavelength pulse wave signals, from pulse wave signals having other wavelengths among the plurality of wavelengths.

23. The apparatus of claim 21, wherein the processor is further configured to measure bio-information of the object by using the multi-wavelength pulse wave signal and the contact pressure signal.

24. A case apparatus for accommodating a bio-information measuring apparatus, the case apparatus comprising:
    a main body configured to accommodate the bio-information measuring apparatus, the main body comprising a guide groove that exposes a pulse wave sensor of the bio-information measuring apparatus;
    a position sensor disposed around the guide groove and configured to obtain a contact position of an object which comes into contact with the pulse wave sensor of the bio-information measuring apparatus, the position sensor comprising at least two electrode parts disposed on at least two opposing positions of the guide groove;
    a processor which is embedded in the main body, the processor configured to compare at least one from among an impedance and a capacitance, measured at each of the at least two electrode parts when the object comes into contact with the pulse wave sensor, and obtain contact position information from a result of comparison, the contact position information indicating whether the object is positioned on a center of the guide groove or whether the object leans toward a side of the guide groove while in contact with the pulse wave sensor; and a communicator circuit configured to transmit the contact position information to the bio-information measuring apparatus.

\* \* \* \* \*